US005766614A

United States Patent [19]

Yong

[11] Patent Number: 5,766,614
[45] Date of Patent: Jun. 16, 1998

[54] BURN TREATMENT COMPOSITIONS CONTAINING HERBAL MIX

[76] Inventor: Liu Yong, 2570 S. Dayton Way, Apt. #F304, Denver, Colo. 80231-3980

[21] Appl. No.: 821,211

[22] Filed: Mar. 20, 1997

[51] Int. Cl.$^6$ .................................................. A61K 35/78
[52] U.S. Cl. .......................... 424/401; 514/944; 514/969; 514/887; 514/844; 424/DIG. 13
[58] Field of Search ........................... 424/195, 195.1, 424/73, 74, 443, 401

[56] References Cited

U.S. PATENT DOCUMENTS

| | | |
|---|---|---|
| 4,276,281 | 6/1981 | Crikelair . |
| 4,318,906 | 3/1982 | Llopart ................................ 424/195 |
| 4,393,045 | 7/1983 | Henderson . |
| 4,837,019 | 6/1989 | Goergalas . |
| 4,839,159 | 6/1989 | Winter et al. . |
| 5,166,132 | 11/1992 | Gordon . |
| 5,221,533 | 6/1993 | Perlman ................................ 424/73 |
| 5,244,662 | 9/1993 | Han et al. ........................... 424/195.1 |
| 5,382,431 | 1/1995 | Pickart . |
| 5,384,125 | 1/1995 | DiPippo et al. ..................... 424/443 |
| 5,405,608 | 4/1995 | Xu ........................................ 424/195.1 |
| 5,411,733 | 5/1995 | Hozumi et al. ..................... 424/195.1 |
| 5,466,452 | 11/1995 | Whittle ................................. 424/195.1 |
| 5,468,492 | 11/1995 | Szaloki et al. ...................... 424/195.1 |
| 5,567,419 | 10/1996 | Togiya et al. ....................... 424/74 |
| 5,595,743 | 1/1997 | Wu ........................................ 424/195.1 |

*Primary Examiner*—Thurman K. Page
*Assistant Examiner*—Brian K. Seidleck

[57] ABSTRACT

A new Burn Treatment Composition which provides healing to the skin of people who have received burns or are afflicted with other skin complications that require healing. The inventive device includes effective amounts of Chinese rhubarb; calcium hydroxide; sanguisorba officinalis rhizome; common camphor; coptis chinensis rhizome; phellodendron amurense bark and oldenlandia diffusa roxd.

11 Claims, No Drawings

BURN TREATMENT COMPOSITIONS CONTAINING HERBAL MIX

BACKGROUND OF THE INVENTION

1. Field of the Invention

The present invention relates to skin treatment compositions and more particularly pertains to a new Burn Treatment Composition which provides healing to the skin of people who have received burns or are afflicted with other skin complications that require healing.

2. Description of the Prior Art

The use of skin treatment compositions is well known in the prior art. More specifically, skin treatment compositions which have devised and utilized are known to consist basically of familiar, expected and obvious elements, notwithstanding the myriad of compositions encompassed by the crowded prior art which have been developed for the fulfillment of countless objectives and requirements.

Known prior art skin treatment compositions include U.S. Pat. No. 4,276,281; U.S. Pat. No. 4,839,159; U.S. Pat. No. 4,837,019; U.S. Pat. No. 5,166,132; U.S. Pat. No. 5,382,431; and U.S. Pat. No. 4,393,045.

While these compositions may fulfill their respective, particular objectives and requirements, the aforementioned patents do not disclose a new Burn Treatment Composition. Advantageously, the present invention teaches the mixture of various kind of herbs that form a compositions used to provide healing to the skin, especially human skin that has been burned by exposure to heat.

In these respects, the Burn Treatment Composition according to the present invention substantially departs from the conventional compositions of the prior art, and in so doing provides compositions primarily developed for the purpose of effectively inhibiting the growth of germs on a treated area of human skin and at the same time, improving the healing growth of skin cells.

SUMMARY OF THE INVENTION

In view of the foregoing disadvantages inherent in the known types of skin treatment compositions now present in the prior art, the present invention provides a new Burn Treatment Composition wherein the same can be utilized for effectively providing healing to the skin of people who have received burns or are afflicted with other skin complications that require healing.

The general purpose of the present invention, which will be described subsequently in greater detail, is to provide a new Burn Treatment Composition, and methods of applying such, which have many of the advantages of skin treatment compositions mentioned heretofore and many novel features that result in a new Burn Treatment Composition which is not anticipated, rendered obvious, suggested, or even implied by any of the prior art skin treatment compositions, either alone or in any combination thereof.

Generally the present invention discloses unique compositions used to provide healing to the skin of people who have received burns or are afflicted with other skin complications that require healing. The unique composition of the present invention comprises, generally, effective amounts of Chinese rhubarb; calcium hydroxide; sanguisorba officinalis rhizome; common camphor; coptis chinensis rhizome; phellodendron amurense bark and oldenlandia diffusa roxd.

Since the present invention may be formulated into creams, lotions, gels, aerosols and the like, other optional ingredients may be added to the essential ingredients of the present invention. These optional ingredients may include but are not limited to fillers, emulsifiers, thickeners, emollients, fragrances and dyes.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DETAILED DESCRIPTION OF THE INVENTION

A unique combination of ingredients has been discovered that advantageously provides desirable skin treatment compositions. When mixed, the ingredients of the present invention advantageously form compositions that when applied to the skin of humans are generally effective in promoting healing of the skin. Typically, the compositions of the present invention can be safely used to provide desirable results generally on most parts of the body.

Essential Components

The compositions of the present invention are generally used on human's skin to promote healing from burns and other skin problems. The composition includes certain essential components or ingredients present in effective amounts. These essential ingredients include Chinese rhubarb; calcium hydroxide; sanguisorba officinalis rhizome; common camphor; coptis chinensis rhizome, phellodendron amurense bark and oldenlandia diffusa roxd. The amounts of each of the components used in the present invention are all set forth as "parts". The number of "parts" for a particular ingredient indicates the relative amount of that particular ingredient in the composition with respect to the number of parts of the other ingredients present in the composition, and does not represent the percent by weight of the ingredient in the composition.

The Chinese rhubarb of the present invention is available in several varieties such as rheum palmatum, rheum tanguticum and rheum officinale. In a preferred composition of the present invention, the preferred amount of Chinese rhubarb is present in an amount of about 60 to about 30 parts of the ingredient. When the other varieties are used, the relative amount of this ingredient in the composition should be increased. Therefore, when rheum palmatum and rheum tanguticum are used in the present invention, the amount preferably ranges from about 100 parts to about 60 parts of this ingredient. When rheum officinale is used, the amount preferably ranges from about 150 parts to about 90 parts. The presence of Chinese rhubarb in the composition, especially in the preferred amount ranges, contributes advantageous properties to the present invention.

Calcium Hydroxide, also known as slaked lime, comprises an essential ingredient of the present invention. Calcium hydroxide is present preferably in an amount of about 100 parts to about 70 parts.

Sanguisorba officinalis rhizome, also known as garden burnet rhizome, provides additional advantageous properties to the composition of the present invention. In the preferred compositions, the amount of sanguisorba officinalis rhizome is present in an amount ranging from about 5 parts to about 10 parts.

Another ingredient that provides beneficial properties to the present invention is common camphor. Camphor is also available from several derivatives, such as, for example, camphor from dryoblanops aromatica, borneol camphor, malayan camphor and barus. The preferred amount of camphor in the present invention ranges from about 2 parts to about 4 parts.

Advantageously, coptis chinensis rhizome, also known as coptis japonica rhizome, provides beneficial properties to the present invention. In a preferred composition, coptis chinensis rhizome is present in an amount of about 3 parts to about 5 parts.

Yet still another ingredient of the present invention is phellodendron amurense bark, also known as phellodendron Chinese scineid bark. The bark provides advantageous properties to the present invention. In a preferred composition, the bark is present in an amount of about 3 to about 6 parts.

The oldenlandia diffusa roxd is a beneficial ingredient of the present invention. Oldenlandia diffusa roxd is preferably present in the present invention in an amount of about 2 parts to about 4 parts.

Optional Ingredients

Advantageously, the present invention can generally be formulated with optional ingredients to further customize it. These ingredients will generally be used in amounts that do not alter the desired properties of the system. Ingredients that may be added to allow the present invention to be used in different forms, such as creams, gels, lotions and so forth. These ingredients include fillers such as chalk, magnesium oxide and carbonate, clay, talc, fused silica, and mixtures thereof, present in amount of about 0 parts to about 10 parts.

Thickeners could include natural and synthetic types. The thickeners used can include but are not limited to xanthan, karaya, guar gum, clay tragacanth various cellulostic materials such as starches. The thickeners can be present in an amount of about 0 parts to about 5 parts.

The foregoing is therefore considered as illustrative only of the principles of the invention. Further, it should be understood that since numerous modifications and changes will readily occur to those skilled in the art, it is not desired to limit the invention to the exact combinations and ingredients shown and described, and accordingly, all suitable modifications and equivalents may be resorted to, falling within the scope of the invention.

The following non-limiting examples, which include the best mode, are set forth to illustrate the present invention.

EXAMPLE 1

About 80 parts of slaked lime was placed in a clean beaker and heated with continued stirring for about 15 minutes at 212° F. Then, about 50 parts of Chinese rhubarb was added and the stirring continued for about another 30 minutes. About 10 parts of sanguisorba officinalis rhizome was added with about 2 parts of common camphor, about 3 parts of coptis chinensis rhizome, about 3 parts of phellodendron amurense bark and about 4 parts of oldenlandia diffusa roxd were added and the temperature was decreased to about 180° F. Heating and mixing continued for about 30 minutes. The mixture was cooled and ground to a fine powder. The ointment was made by using the fine powder in a ratio of about 1 part of powder to about 5 parts of sesame oil.

EXAMPLE 2

About 90 parts of slaked lime was placed in a clean beaker and heated with continued stirring for about 15 minutes at 212° F. Then, about 60 parts of Chinese rhubarb was added and the stirring continued for about another 30 minutes. About 9 parts of sanguisorba officinalis rhizome was added with about 3 parts of common camphor, about 5 parts of coptis chinensis rhizome, about 6 parts of phellodendron amurense bark and about 2 parts of oldenlandia diffusa roxd were added and the temperature was decreased to about 180° F. Heating and mixing continued for about 30 minutes. The mixture was cooled and ground to a fine powder. The ointment was made by using the fine powder in a ratio of about 1 part of powder to about 5 parts of sesame oil.

EXAMPLE 3

About 100 parts of slaked lime was placed in a clean beaker and heated with continued stirring for about 15 minutes at 212° F. Then, about 40 parts of Chinese rhubarb was added and the stirring continued for about another 30 minutes. About 5 parts of sanguisorba officinalis rhizome was added with about 4 parts of camphor, about 3 parts of coptis chinensis rhizome, about 3 parts of phellodendron amurense bark and about 3 parts of oldenlandia diffusa roxd were added and the temperature was decreased to about 180° F. Heating and mixing continued for about 30 minutes. The mixture was cooled and ground to a fine powder. The ointment was made by using the fine powder in a ratio of about 1 part of powder to about 5 parts of sesame oil.

EXAMPLE 4

About 70 parts of slaked lime was placed in a clean beaker and heated with continued stirring for about 15 minutes at 212° F. Then, about 30 parts of Chinese rhubarb was added and the stirring continued for about another 30 minutes. About 10 parts of sanguisorba officinalis rhizome was added with about 2 parts of camphor, about 4 parts of coptis chinensis rhizome, about 4 parts of phellodendron amurense bark and about 2 parts of oldenlandia diffusa roxd were added and the temperature was decreased to about 180° F. Heating and mixing continued for about 30 minutes. The mixture was cooled and ground to a fine powder. The ointment was made by using the fine powder in a ratio of about 1 part of powder to about 5 parts of sesame oil.

The compositions above were applied to an area of burned skin, and left on the burned skin for approximately twelve (12) hours. The composition was removed after this time with a 3% peroxide solution and a fresh application of the composition to the area of burned skin was done. For a mild wound, healing was completed within about a week. More severe wounds healed within about one to four weeks.

What is claimed as being new and desired to be protected by Letters Patent of the United States is as follows:

1. A Burn Treatment Composition comprising:
   (a) Chinese rhubarb
   (b) calcium hydroxide;
   (c) sanguisorba officinalis rhizome;
   (d) common camphor;
   (e) coptis chinensis rhizome;
   (f) phellodendron amurense bark; and
   (g) oldenlandia diffusa roxd in an amount effective to treat human skin that has been burned by exposure to heat.

2. The Burn Treatment Composition of claim 1 wherein the Chinese rhubarb is selected from the group consisting of: rheum palmatum, rheum tanguticum, and rheum officinale and mixtures thereof.

3. The Burn Treatment Composition of claim 1 wherein the Chinese rhubarb is present in an amount of about 30 parts to about 60 parts.

4. The Burn Treatment Composition of claim 1 wherein the calcium hydroxide is present in an amount of about 70 parts to about 100 parts.

5. The Burn Treatment Composition of claim 1 wherein the sanguisorba officinalis rhizome is present in an amount of about 5 parts to about 10 parts.

6. The Burn Treatment Composition of claim 1 wherein the common camphor is present in an amount of about 2 parts to about 4 parts.

7. The Burn Treatment Composition of claim 1 wherein the coptis chinensis rhizome is present in an amount of about 3 parts to about 5 parts.

8. The Burn Treatment Composition of claim 1 wherein the phellodendron amurense bark is present in an amount of about 3 parts to about 6 parts.

9. The Burn Treatment Composition of claim 1 wherein the oldenlandia diffusa roxd is present in an amount of about 2 parts to about 4 parts.

10. The Burn Treatment Composition of claim 1 which further comprises an ingredient selected from the group consisting of fillers emulsifiers, and thickeners.

11. A Burn Treatment Composition comprising:
   (a) about 50 parts of Chinese rhubarb
   (b) about 80 parts of calcium hydroxide;
   (c) about 10 parts of sanguisorba officinalis rhizome;
   (d) about 2 parts of common camphor;
   (e) about 3 parts of coptis chinensis rhizome;
   (f) about 3 parts of phellodendron amurense bark; and
   (g) about 4 parts of oldenlandia diffusa roxd.

* * * * *